(12) United States Patent
Chitre et al.

(10) Patent No.: US 8,538,555 B1
(45) Date of Patent: Sep. 17, 2013

(54) CARDIAC ACCESS METHODS AND APPARATUS

(75) Inventors: Yougandh Chitre, Santa Clara, CA (US); Gene A. Bornzin, Simi Valley, CA (US); John R. Helland, Tallahassee, FL (US); Eric Falkenberg, Las Vegas, NV (US); Kevin L. Morgan, Simi Valley, CA (US); Sheldon Williams, Green Valley, CA (US); Michael Yang, Thousand Oaks, CA (US); Andrew W. McGarvey, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 201 days.

(21) Appl. No.: 12/973,810

(22) Filed: Dec. 20, 2010

Related U.S. Application Data

(62) Division of application No. 11/753,484, filed on May 24, 2007, now Pat. No. 7,881,810.

(51) Int. Cl.
*A61N 1/00* (2006.01)

(52) U.S. Cl.
USPC .......................................................... 607/129

(58) Field of Classification Search
USPC .......................................................... 607/129
See application file for complete search history.

(56) References Cited

U.S. PATENT DOCUMENTS

| | | | |
|---|---|---|---|
| 4,865,037 A | 9/1989 | Chin et al. | |
| 4,884,567 A | 12/1989 | Elliott et al. | |
| 4,946,457 A * | 8/1990 | Elliott | 606/1 |
| 4,991,578 A | 2/1991 | Cohen et al. | |
| 4,998,975 A * | 3/1991 | Cohen et al. | 607/5 |
| 5,033,477 A | 7/1991 | Chin et al. | |
| 5,071,428 A | 12/1991 | Chin et al. | |
| 5,336,252 A | 8/1994 | Cohen | |
| 5,968,010 A | 10/1999 | Waxman et al. | |
| 6,423,051 B1 | 7/2002 | Kaplan et al. | |
| 6,613,062 B1 | 9/2003 | Leckrone et al. | |
| 2003/0212446 A1 | 11/2003 | Kaplan et al. | |
| 2004/0015193 A1 | 1/2004 | Lamson et al. | |
| 2004/0215168 A1 | 10/2004 | Verrier et al. | |
| 2004/0216748 A1 | 11/2004 | Chin | |
| 2005/0102003 A1 | 5/2005 | Grabek et al. | |
| 2005/0113901 A1 * | 5/2005 | Coe et al. | 607/130 |
| 2005/0165466 A1 | 7/2005 | Morris et al. | |
| 2006/0116746 A1 | 6/2006 | Chin | |

OTHER PUBLICATIONS

Restriction Requirement, mailed Sep. 25, 2009—Parent U.S. Appl. No. 11/753,484.
NonFinal Office Action, mailed Feb. 3, 2010—Parent U.S. Appl. No. 11/753,484.
Final Office Action, mailed Jul. 21, 2010—Parent U.S. Appl. No. 11/753,484.
Notice of Allowance, mailed Nov. 15, 2010—Parent U.S. Appl. No. 11/753,484.

* cited by examiner

*Primary Examiner* — Christopher D Koharski
*Assistant Examiner* — Philip Edwards

(57) ABSTRACT

A chamber or vasculature of a heart may be accessed via the pericardial space of the heart. Initially, the pericardial space may be accessed via a transmyocardial approach or a subxiphoid approach. A lead or other implantable apparatus may thus be routed into the pericardial space, through myocardial tissue and into the chamber or vasculature. The lead or other apparatus may be used to sense activity in or provide therapy to the heart.

8 Claims, 15 Drawing Sheets

CARDIAC ACCESS METHODS AND APPARATUS

CROSS REFERENCE TO RELATED APPLICATIONS

This application is a division of copending U.S. patent application Ser. No. 11/753,484, filed May 24, 2007, titled "Cardiac Access Methods and Apparatus"

TECHNICAL FIELD

This application relates generally to implantable cardiac devices and, in some embodiments, to methods of accessing the pericardial space and other areas of a heart.

BACKGROUND

Implantable cardiac devices are used to treat a patient's heart that does not function normally due to, for example, a genetic or acquired condition. A typical implantable cardiac device may perform one or more functions including sensing signals generated in the heart, pacing the heart to maintain regular contractions and providing defibrillation shocks to the heart.

Upon implant an implantable cardiac device is connected to one or more implantable cardiac leads. These cardiac leads are routed from the implanted cardiac device through the patient's body to the heart. Each cardiac lead includes one or more electrodes that are positioned adjacent to tissue at specific locations within the heart to enable sensing of cardiac signals or application of cardiac stimulation signals at those locations. For example, a typical implantable cardiac lead may include a bipolar electrode at its distal end for sensing cardiac signals and generating pacing signals and a coil electrode for generating shocking signals.

Various techniques have been used to implant a cardiac device and associated cardiac leads. An endocardial implantation technique generally involves gaining access to the interior of the heart via the venous return and implanting one or more leads within the heart. For example, an implantable device including circuitry for sensing signals from and generating stimulation signals for the heart may be subcutaneously implanted in the pectoral region of the patient. Leads connected to the device are routed from the device through a vein to the right side of the heart. A distal end of the lead is then passively or actively attached to an inner wall of the heart.

In practice, it may not be possible to position an electrode at a location that provides a desired level of sensing and pacing performance. For example, the implant location for an implantable cardiac lead depends on various factors such as the anatomy of the patient's venous system and the need to avoid incidental stimulation of the patient's anatomy. Here, factors such as a coronary sinus obstruction, the absence of a suitable cardiac vein for lead access, high threshold levels or potential phrenic nerve stimulation may prohibit the use of a traditional transvenous approach for the implantation of left ventricle leads in patients with cardiac heart failure ("CHF") that are in need of cardiac resynchronization ("CRT") therapy.

An epicardial implantation technique generally involves implanting leads at an outer layer of the heart (on the epicardium). Traditionally, this technique has been proposed for implanting coils across the heart to induce defibrillation shocks. Here, an implantable device including the defibrillation circuitry may be implanted in the abdominal region or the pectoral region of the patient. Sensing and stimulation leads are thus routed from the device to appropriate or preferred sites on the epicardium via an appropriate path.

SUMMARY

A summary of various aspects and/or embodiments of an apparatus constructed or a method practiced according to the invention follows. For convenience, one or more embodiments of an apparatus constructed or a method practiced according to the invention may be referred to herein simply as an "embodiment."

The invention relates in some aspects to accessing a chamber or vasculature of a heart from the pericardial space of the heart. For example, a lead or other implantable apparatus may be routed from the pericardial space through myocardial tissue and into an inner chamber or vasculature of the heart. The lead or other apparatus may then be used to sense activity in or provide therapy to the heart. In particular, activity may be sensed and/or therapy may be applied from a location within the chamber or vasculature.

The invention relates in some aspects to techniques for fixing the lead or apparatus to heart tissue. For example, active or passive fixation mechanisms may be used to attach the lead to or fix the lead against heart tissue. In some embodiments a distal portion of a lead may be fixed to an inner wall of a chamber or vasculature. In some embodiments the lead may be fixed to an epicardial layer and/or an outer pericardial layer.

The invention relates in some aspects to accessing the pericardial space of a heart. For example, the pericardial space may be accessed via a transmyocardial approach or a subxiphoid approach. In the former case, an apparatus may be routed transvenously to the right side of the heart then routed through myocardial tissue to the pericardial space. For example, the apparatus may be routed through an outer wall of the right atrium or the right ventricle.

In some aspects a delivery apparatus may be used to create a hole in a heart wall. In some embodiments the delivery apparatus may be adapted to determine when a piercing member has passed through the heart wall and into the pericardial space.

In some aspects a lead or apparatus delivered via a transmyocardial approach may be used to provide therapy to the heart. For example, in some embodiments the lead or apparatus may be used to deliver a mechanical constriction apparatus that prevents or reduces dilation of cardiac tissue associated with CHF or a myocardial infarction ("MI").

BRIEF DESCRIPTION OF THE DRAWINGS

These and other features, aspects and advantages of the invention will be more fully understood when considered with respect to the following detailed description, appended claims and accompanying drawings, wherein:

FIG. 1, including

FIG. 2, including

FIG. 3, including

FIG. 4, including

FIG. 5, including

FIG. 11, including

FIG. 13, including

Figure 1A:
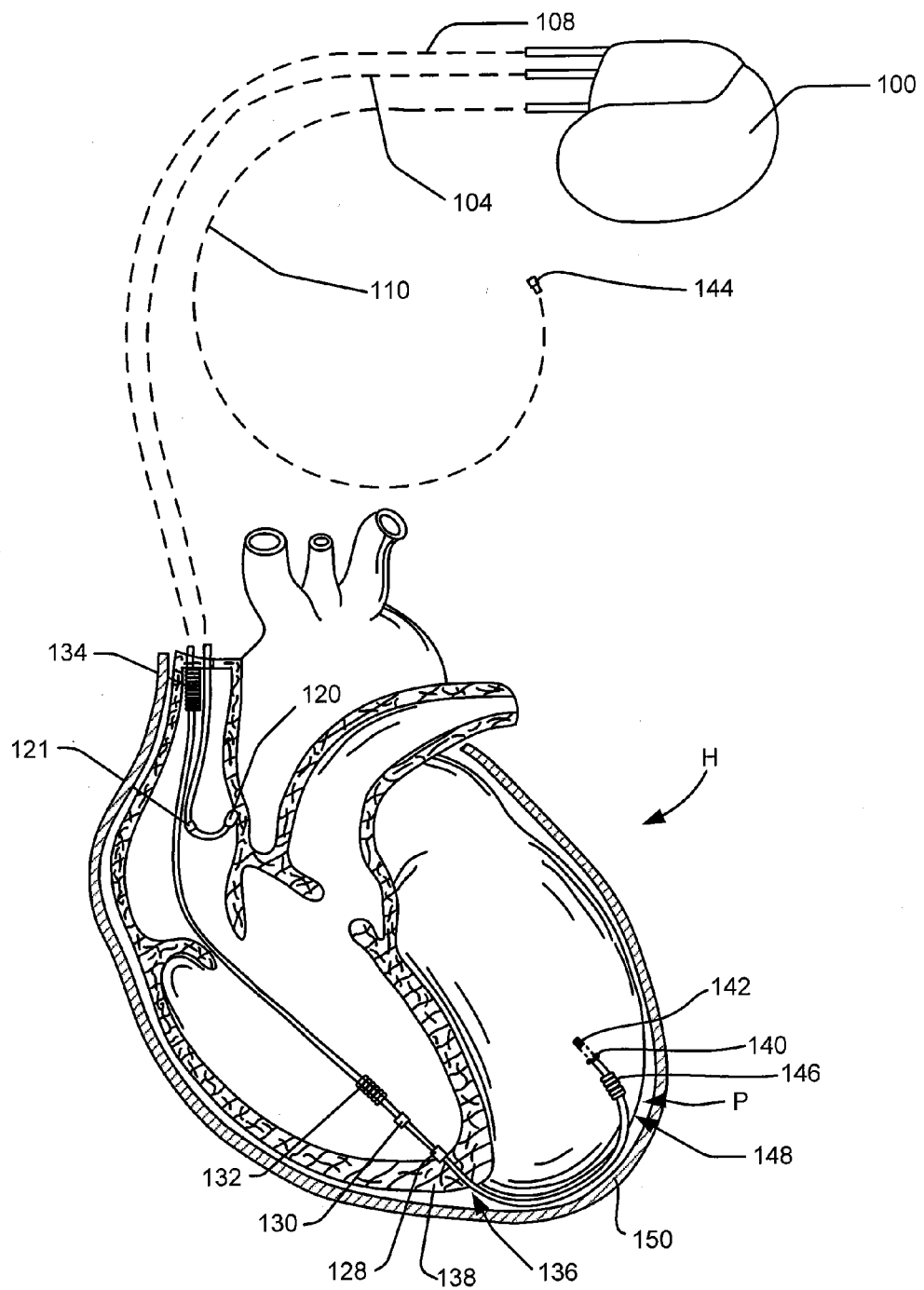
FIGS. 1A and 1B, depicts simplified diagrams of an embodiment of an implantable stimulation device in electrical communication with several leads implanted in a patient's heart for delivering multi-chamber sensing and stimulation therapy.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the details and components of a given body part, apparatus or method. Finally, like reference numerals may be used to denote like features throughout the specification and figures.

DETAILED DESCRIPTION

The invention is described below, with reference to detailed illustrative embodiments. It will be apparent that the invention may be embodied in a wide variety of forms, some of which may appear to be quite different from those of the disclosed embodiments. Consequently, the specific structural and/or functional details disclosed herein are merely representative and do not limit the scope of the invention. For example, based on the teachings herein one skilled in the art should appreciate that the various structural and/or functional details disclosed herein may be incorporated in an embodiment independently of any other structural and/or functional details. Thus, an apparatus may be implemented and/or a method practiced using any number of the structural and/or functional details set forth in any disclosed embodiment(s). Also, an apparatus may be implemented and/or a method practiced using other structural and/or functional details in addition to or other than the structural and/or functional details set forth in any disclosed embodiment(s).

FIG. 1A illustrates an exemplary implantable cardiac device 100 in electrical communication with a patient's heart H by way of implantable cardiac leads 104 and 108, suitable for providing multi-chamber sensing and cardiac stimulation (e.g., pacing and/or shock therapy). Here, a portion of the heart H is shown in a partially cutaway view to more clearly illustrate the routing of the leads 104 and 108 within the heart H. To provide sensing and/or cardiac stimulation in the right atrium, the cardiac device 100 is coupled to the lead 104, including a bi-polar electrode pair 120 and 121. To provide additional right-side sensing and/or cardiac stimulation the cardiac device 100 is coupled to the lead 108, including a bipolar electrode pair 128 and 130, implanted in the right ventricle of the heart H.

In the example of FIG. 1A, a distal portion of the lead 108 is routed through a hole 136 in myocardial tissue of an outer wall 138 of the heart H and into a pericardial space P that exists between an epicardial layer 148 and an outer pericardial layer 150 of the heart H. From here, the distal end of the lead 108 is routed through another hole 140 in myocardial tissue of an outer wall of the heart H to an inner chamber (e.g., the left ventricle) or vasculature of the heart H. The distal portion of the lead 108 includes one or more electrodes for sensing or stimulating the heart. For example, the lead 108 may include an electrode 142 and a shocking coil 146.

Cardiac devices 100 supporting various functionality may be used in conjunction with the embodiments that are described herein. For example, the device 100 may comprise a stimulation device such as a cardioverter defibrillator or any other suitable implantable cardiac device. It is to be appreciated and understood that other cardiac devices, including those that are not necessarily implantable, may be used in conjunction with a lead or other apparatus in accordance with the teachings herein.

In FIG. 1A, the implantable right ventricular lead 108 also includes a right ventricular (RV) coil electrode 132 and superior vena cava (SVC) coil electrode 134. The right ventricular lead 108 is transvenously inserted into the heart H to place the electrode 128 in the right ventricular apex and so that the RV coil electrode 132 will be positioned in the right ventricle and the SVC coil electrode 134 will be positioned in the superior vena cava. Accordingly, the lead 108 is capable of sensing or receiving cardiac signals, and delivering stimulation in the form of pacing and shock therapy to the right and left ventricles.

Device 100 is also shown in electrical communication with a lead 110 including one or more components 144 such as a physiologic sensor. A component 144 may be positioned in, near or remote from the heart H.

It should be appreciated that the device 100 may connect to leads and/or components other than those specifically shown. For example, two leads may be used instead of the single lead 108. Here, one lead may be implanted in the right ventricle to provide right ventricle sensing and/or stimulation while the other lead is routed through an outer wall of one of the chambers of the heart H and into the pericardial space P. In addition, the leads connected to the device 100 may include components other than those specifically shown. For example, a lead may include other types of electrodes, sensors or devices that serve to otherwise interact with a patient or the surroundings.

Figure 1B:
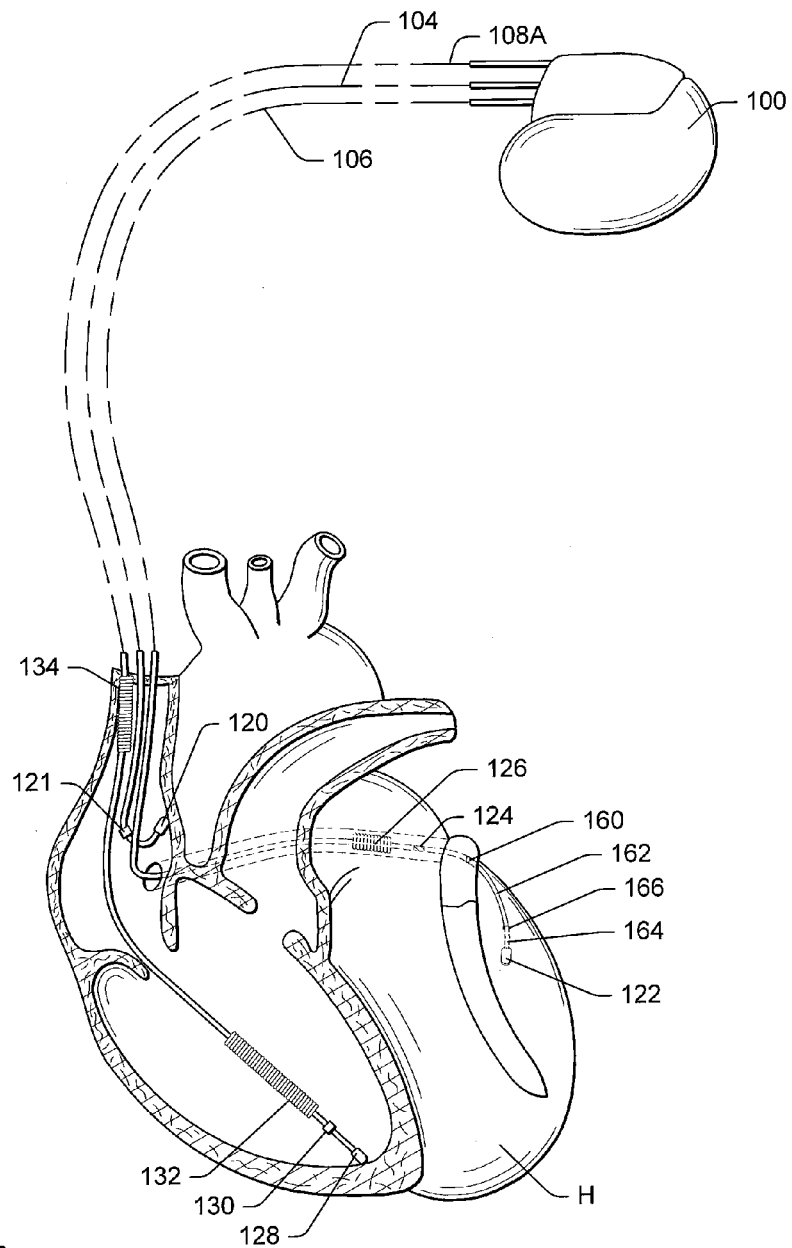

FIG. 1B illustrates an embodiment where the device 100 is connected to a coronary sinus lead 106, a right atrial lead 104 and a right ventricular lead 108A. In this example, the distal end of the lead 108A is implanted in the right ventricle and does not enter the pericardial space.

The coronary sinus lead 106 may be designed for placement in the coronary sinus region via the coronary sinus for positioning one or more electrodes adjacent to the left atrium or some other area of the heart. As used herein, the phrase "coronary sinus region" refers to the vasculature of the left ventricle, including any portion of the coronary sinus, the great cardiac vein, the left marginal vein, the left posterior ventricular vein, the middle cardiac vein, the small cardiac vein or any other cardiac vein accessible by the coronary sinus.

The coronary sinus lead 106 may be designed to receive atrial and other cardiac signals and to provide left atrial pacing therapy using, for example, a left atrial ring electrode 124; and provide shocking therapy using, for example, a left atrial coil electrode 126 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

The coronary sinus lead 106 also may be routed through the pericardial space and back into an inner chamber or vasculature of the heart H. For example, in FIG. 1B a distal portion of the lead 106 is routed through a hole 160 created in a coronary sinus region and into the pericardial space (as represented by a non-dashed portion 162 of the lead 106). From here, a more distal portion of the lead 106 (as represented by a dashed portion 164) is routed through another hole 166 created in myocardial tissue of an outer wall of the heart H to an inner chamber (e.g., the left ventricle) or vasculature of the heart H. The distal end of the lead 106 or some other portion of the lead may include one or more electrodes for sensing or stimulating the heart. For example, the lead 106 may include a tip electrode 122 and, optionally, a ring electrode (not shown) for sensing or pacing (e.g., in the left ventricle).

Figure 2A:
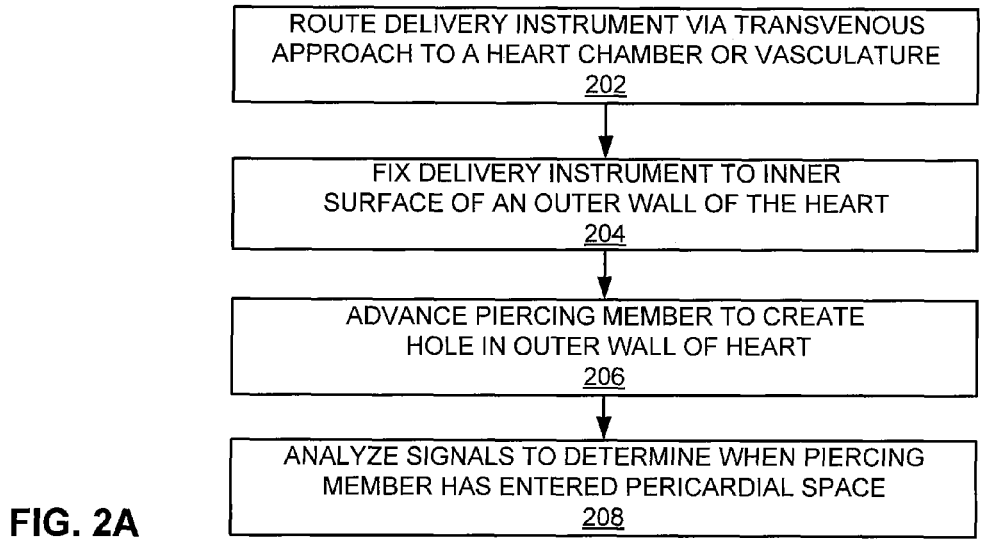
FIGS. 2A and 2B, is a flowchart of an embodiment of operations that may be performed to access the pericardial space and a chamber or vasculature of the heart.
Figure 2B:
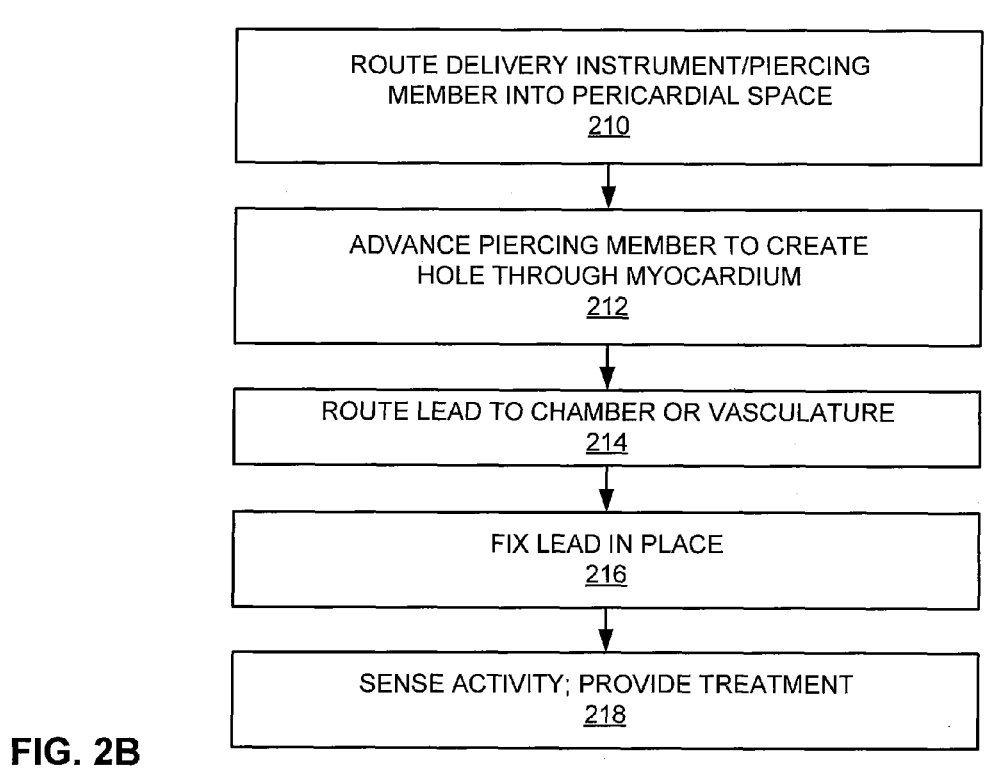

FIG. 2 illustrates an embodiment of operations that may be performed to access the pericardial space and an inner chamber or vasculature of the heart. FIG. 2A relates, in general, to a transmyocardial method of accessing the pericardial space. FIG. 2B relates, in general, to a transpericardial method of accessing an inner chamber or vasculature of the heart. For convenience, the operations of FIG. 2 may be described in conjunction with specific embodiments and/or components described herein. It should be appreciated, however, that these operations may be performed in conjunction with or using other components.

As represented by block 202 in FIG. 2A, a delivery apparatus is routed transvenously to an interior space of the heart. For example, the distal portion of the delivery apparatus may be routed from an implant site for the device 100 (e.g., in the pectoral region) through a vein and into a chamber on the right side of the heart. The distal end of the delivery apparatus may then be positioned against an outer wall of the chamber (e.g., right atrium or right ventricle) or some other space of the heart. Here, the distal end is placed at a location where a lead or another apparatus is to be routed through a hole to be created in the heart wall and into the pericardial space. For example, when entering the pericardial space from the right atrium, the hole may be created in the vicinity of the right atrial appendage. In other embodiments a hole may be created through some other wall in some other interior space of the heart. For example, in some embodiments access to the pericardial space may be gained via the coronary sinus as illustrated in FIG. 1B.

In some embodiments it may prove advantageous to access the pericardium via the right ventricle (e.g., as depicted in FIG. 1A). In some embodiments, when entering the pericardial space from the right ventricle, the hole may be created in the vicinity of the right ventricular apex. In this area, the outer wall is relatively thin and contains a relatively minimal amount of vasculature (e.g., arteries or veins). Hence, any risk of causing damage by puncturing in this area may be relatively low. Moreover, creating a hole in this area provides a relatively direct (e.g., substantially straight) path from the access vein. Given this relatively direct line of access, it may be easier to bore a hole through the heart wall (e.g., using a relatively straight and stiff needle-like apparatus or a screw type apparatus).

Figure 3A:
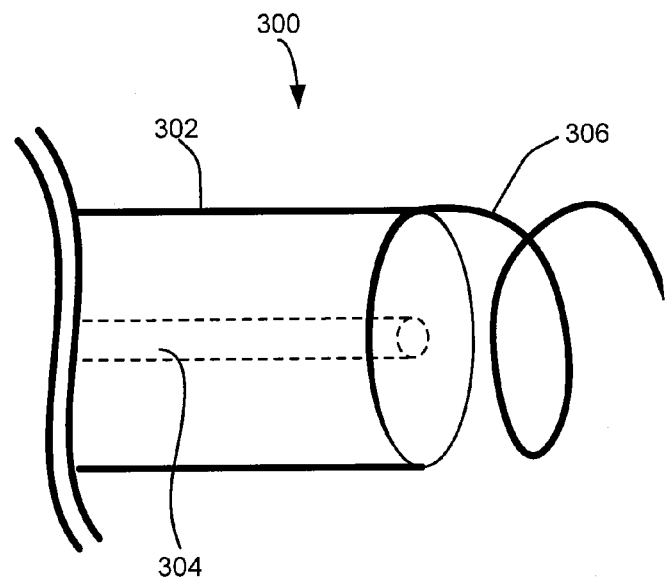
FIGS. 3A and 3B, is a simplified diagram of an apparatus for delivering a lead or other apparatus to the pericardial space.

FIG. 3A illustrates a distal portion of one embodiment of a delivery instrument 300 (e.g., a catheter or sheath). The delivery instrument 300 includes an elongated body 302 defining one or more internal lumens (hereafter referred to as "lumen 304") adapted to slideably contain a lead or other apparatus (hereafter referred to as "the lead") that is to be delivered to the pericardial space. In accordance with conventional implantable lead practice, a proximal portion (not shown) of the delivery instrument 300 may include appropriate structure to enable the delivery instrument 300 to be routed through a vein and manipulated as necessary (e.g., via a stylet).

As represented by block 204, a distal portion of the delivery instrument 300 may be fixed to an outer wall of the heart (e.g., a wall of a chamber or a vessel of the heart). For example, in some embodiments the delivery instrument 300 may include one or more fixation structures (hereafter referred to as "fixture 306"). In the example of FIG. 3A, the fixture 306 comprises a helix that may be screwed into the heart wall to secure the delivery instrument 300 to the heart wall. It should be appreciated that other types of fixation structures (e.g., tines, barbs, hooks, etc.) may be used to accomplish a similar result.

Figure 3B:
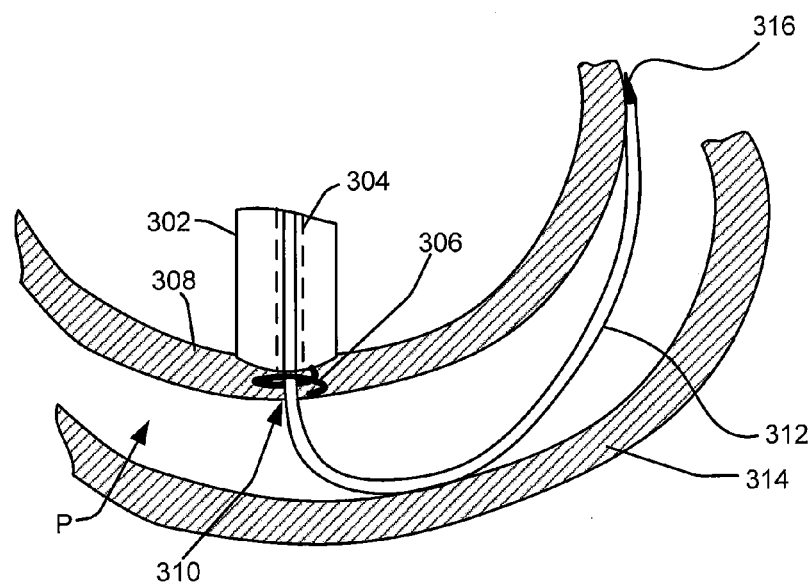

FIG. 3B illustrates, in a cutaway view, an example of how the delivery instrument 300 may be fixed to a wall 308 of the heart. Here, it may be seen that the fixture 306 has been screwed into the heart wall 308 to secure the distal end of delivery instrument 300 against the heart wall 308. Such a fixation technique may prove advantageous when subsequently delivering the lead through the lumen 304 as will be discussed below.

It should be appreciated that various other techniques may be used to route a delivery instrument to a heart wall. For example, in some embodiments this may be accomplished through the use of an elongated sheath or other apparatus (not shown) adapted to be routed through a vein. Such an embodiment may be used, for example, to ensure that the fixture 306 does not impede a smooth delivery of the delivery instrument 300 through the vein. In this case the sheath/apparatus may be initially routed to the heart wall so that the delivery instrument 300 may be routed through the sheath/apparatus to the heart wall.

As represented by block 206, a piercing member associated with the delivery instrument 300 may be advanced to create a hole 310 through the outer wall 308 into the pericardial space P. In the example of FIG. 3B, the piercing member comprises a thin elongated member 312 that is adapted to slide within the lumen 304 of the delivery instrument 300. For example, the member 312 may comprise a stylet, a stiff guidewire, or some other suitable apparatus. For clarity, the portion of the member 312 that is within the delivery instrument 300 is not shown in dashed form as is conventional practice. It should be understood, however, that in some embodiments at least a portion of the member 312 is surrounded by an outer portion of the delivery instrument 300 such that the member extends from a hole (not shown) at the distal end of the lumen 304.

In some embodiments the distal end of the member 312 may include a sharp tip 316 to facilitate puncturing through the heart wall 308. In other embodiments the distal end of the member 312 may be relatively blunt such that the member 312 may be less likely to puncture through an outer pericardial layer 314 and into the thoracic cavity.

In some embodiments a piercing member may be incorporated into the body 302. For example, the distal end of the body 302 may take the form of a point or some other suitable shape. Alternatively, a piercing member may be attached to the distal end of the body 302.

As represented by block 208 in FIG. 2, in some embodiments provisions may be made in an attempt to ensure that the piercing member does not puncture or otherwise damage the outer pericardial layer 314. For example, the delivery instrument, the piercing member, a lead, or some other component may include one or more sensors (e.g., electrodes) that may be used to determine when the piercing member has passed through the hole 310 into the pericardial space P.

Figure 4A:
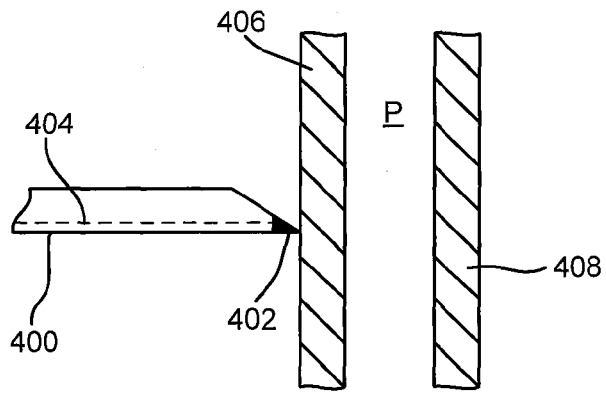
FIGS. 4A-4C, is a simplified diagram of an embodiment of a piercing member of a transmyocardial delivery apparatus employing a sensing element.

FIG. 4 illustrates a distal portion of an embodiment of a piercing member 400 that incorporates one or more electrodes (hereafter, "electrode 402") that may be adapted to sense the position of the piercing member 400 relative to cardiac tissue. For example, the electrode 402 may sense cardiac signals that are provided via a conductor 404 to a device (not shown) that analyzes the cardiac signals. Here, a change in the sensed signals may be used to generate an indication as to the position of the piercing member 400. For example, a change may be sensed when the electrode 402 is in contact with an outer wall 406 of the heart as shown in FIG. 4A as opposed to when the electrode 402 is in the pericardial space P. Similarly, different signals may be sensed when the electrode 402 is in contact with an outer pericardial layer 408.

Figure 4B:
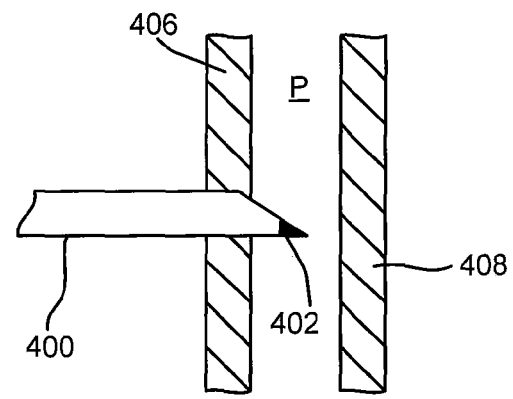
Figure 4C:
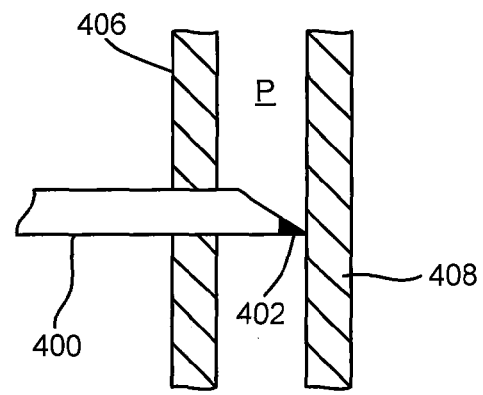

In some embodiments the electrode 402 may comprise a portion of a passive sensor mechanism that detects naturally occurring signals (e.g., cardiac electrical signals). In this case, the device coupled to the conductor 404 at the proximal portion of the piercing member 404 may be adapted to identify a change in a sensed intracardiac electrogram ("IEGM") signal. Here, it may be expected that the IEGM signal may be more attenuated once the electrode 402 passes through the wall 406 (e.g., as shown in FIGS. 4B and 4C). In practice, the electrode 402 may operate in conjunction with one or more other electrodes such as a "can" electrode (not shown).

Alternatively, in other embodiments the electrode 402 may comprise a portion of an active sensor mechanism. For example, the electrode 402 may be used to measure impedance, detect or generate non-naturally occurring signals, or provide some other suitable function, to provide a desired indication. Again, the electrode 402 may operate in conjunction with one or more other electrodes (not shown).

Figure 5A:
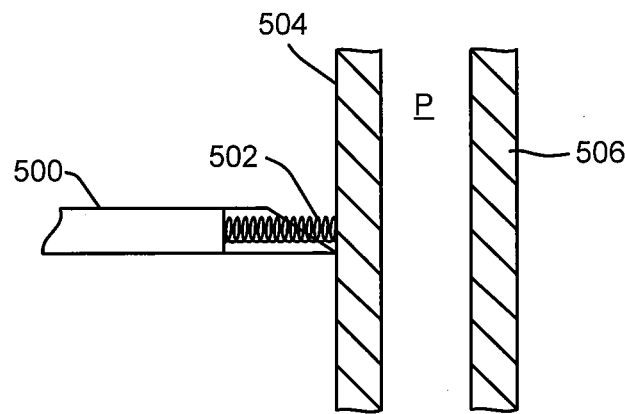
FIGS. 5A and 5B, is a simplified diagram of an embodiment of a piercing member of a transmyocardial delivery apparatus employing a spring element.

FIG. 5 illustrates an embodiment that incorporates a spring-like mechanism to sense the position of a piercing member 500 relative to cardiac tissue. For convenience, only the distal portion of the piercing member 500 is shown in FIG. 5. In this example, a spring 502 is adapted to be compressed into and expand out of a distal end of the piercing member 500. For clarity, the portion of the spring 502 that is within the piercing member 500 is not shown in dashed form as is conventional practice. It should be understood, however, that in some embodiments at least a portion of the spring 502 is surrounded by an outer portion of the piercing member 500 such that the spring extends from a hole (not shown) at the distal end of the piercing member 500.

Figure 5B:
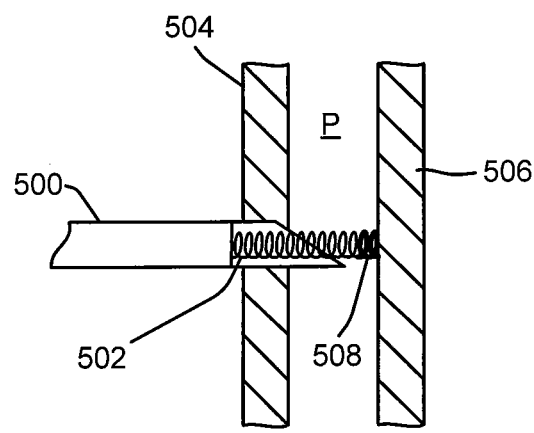

The spring 502 will be at least partially compressed into the piercing member 500 when the distal end of the piercing member 500 is in contact with an outer heart wall 504. For example, a shown in FIG. 5A the spring 502 is compressed when the piercing member 500 is creating a hole in the wall 504. As shown in FIG. 5B, once the distal end of the piercing member 500 advances through the wall 504 and into the pericardial space P, the spring 502 will spring out from the distal end of the piercing member 500. At this point, the distal end of the spring 502 may make contact with an outer pericardial layer 506. Here, the action of the spring 502 against the layer 506 may serve to prevent the piercing member 500 from significantly damaging the layer 506.

Moreover, the action of the spring 502 may serve to provide an indication to the physician controlling the piercing member 500 to stop applying force in the distal direction. For example, the physician may feel a sudden change in tension resulting from the spring action. Alternatively, the distal end of the spring 502 may comprise an electrode 508 that may serve a similar function as the electrode 402 of FIG. 4.

Once a hole has been created in the outer wall of the heart, a lead or other apparatus may be routed through the delivery instrument to the hole and into the pericardial space. As will be discussed in detail below, various components may utilize this pericardial space access technique and various forms of therapy may be applied via these components.

Referring now to FIG. 2B, an example of operations that may be performed to route a lead or apparatus from the pericardial space into an inner chamber or vasculature of the heart will be discussed in some detail. As represented by block 210, a delivery instrument, a piercing member or some other apparatus that may be used to create a hole in heart tissue is routed into the pericardial space. In some embodiments a guidewire or other suitable instrument may initially be routed into the pericardial space and manipulated so that the guidewire takes a desired path through the pericardial space. The delivery instrument, piercing member, etc., may then be routed over the guidewire. In some embodiments the guidewire may have a relatively blunt distal end so that the guidewire will not puncture the outer pericardial layer.

In some cases it may be necessary to use mechanical means (e.g., saline under pressure, a blunt dilator, etc.) to separate layers defining the pericardial space. For example, in some patients there may be fibrosis in the pericardial space that could be separated using a spatula type instrument or mechanical pressure. Alternatively, in some cases it may be possible to traverse around obstacles in the pericardial space.

In some embodiments, the operations of FIG. 2A may precede the operations of FIG. 2B. For example, a piercing member, etc., may be routed via a transvenous approach into a right-side chamber, then into the pericardial space.

In other embodiments access to the pericardial space may be gained by other means. For example, in some embodiments a subxiphoid approach may be used to gain access to the pericardial space. An example of a subxiphoid approach is discussed in more detail later in this disclosure.

As represented by block 212 in FIG. 2B, in some embodiments the piercing member may be advanced through the pericardial space to a location on the epicardial surface where it is desired to reenter the interior of the heart. The piercing member may then be directed into the epicardial surface and through the myocardium to create a hole that passes through the myocardium and into an inner chamber or vasculature of the heart.

Figure 6A:
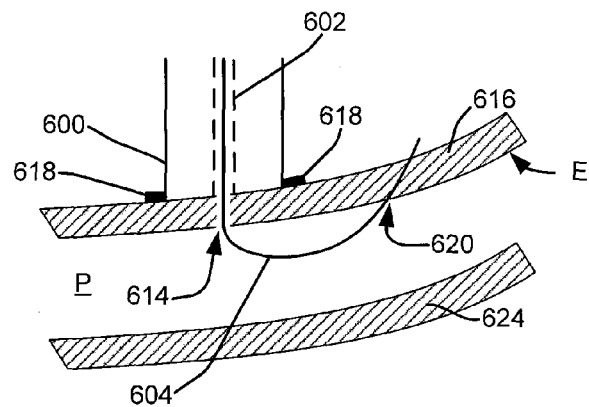
FIG. 6, including FIGS. 6A-6C, consists of several simplified diagrams of various embodiments illustrating creating a hole to gain access to a chamber or vasculature of the heart.
Figure 6B:
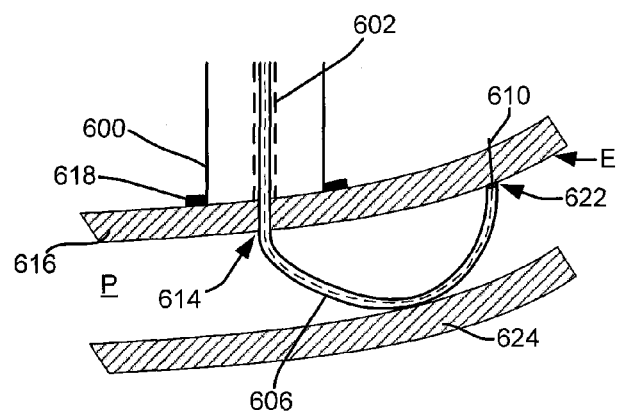
Figure 6C:
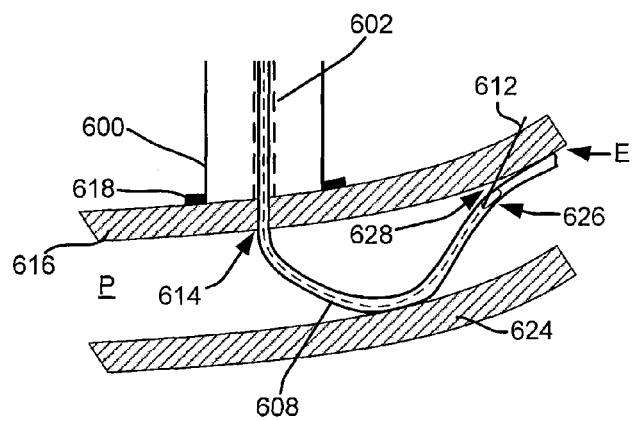

FIG. 6 illustrates several embodiments of components that may be used to create a hole through the myocardium. In these examples a delivery instrument 600 similar to the delivery instrument discussed above in conjunction with FIG. 3 may be used to deliver one or more components (e.g., a guidewire, a piercing member, a lead, etc.) into the pericardial space. To this end, the delivery instrument 600 also includes a lumen 602 for carrying such components. For example, in FIG. 6A a piercing member 604 is adapted to slide within the lumen 602 and exit the distal end of the delivery instrument 600 to gain access to the pericardial space P. Similarly, in FIGS. 6B and 6C smaller delivery instruments 606 and 608 carrying piercing members 610 and 612, respectively, are adapted to slide within the lumen 602 to gain access to the pericardial space.

The piercing member 604 and the delivery instruments 606 and 608 are adapted to enable a physician to effectively route these components to a desired location in the pericardial space P. For example, the proximal portions (not shown) of these components may include handles or include a lumen that accepts a stylet or some other suitable instrument to enable the physician to steer the components through the pericardial space P. In addition, or alternatively, a distal portion of the delivery instrument and/or a component may be bent (e.g., curved) or adapted to bend in a certain direction to facilitate routing the component in a desired direction.

To reduce the complexity of FIG. 6, the holes into and out of the pericardial space are shown relatively close together. This close proximity of the holes may exist, for example, in embodiments where the hole into the pericardial space is in the area of the right ventricle apex while the hole into the myocardium is in the area of the left ventricle apex (e.g., the thin dimple in the apex). It should be understood, however, that in other embodiments there may be a relatively large distance between the holes into and out of the pericardial space.

Referring to FIG. 6A, in some embodiments the piercing member 604 may be predisposed to bend in a particular direction or the piercing member may include a lumen that accepts a guidewire or stylet (not shown) that a physician may use to manipulate the piercing member. In either case, the distal portion of the piercing member 604 may be bent after it passes through a hole 614 created in an outer wall 616 of the heart (e.g., as discussed above in conjunction with FIG. 3). Once the distal end of the piercing member 604 is positioned at a desired location on the epicardial surface E, the physician may push a proximal portion of the piercing member 604 in a distal direction to direct the distal end of the piercing member 604 through the myocardium 616. In this way, the piercing member 604 creates a hole 620 through the myocardium 616.

As discussed above, the delivery instrument 600 may incorporate some form of fixture mechanism 618. For example, hooks, tines, barbs, or some other suitable fixed or deployable mechanism may be used to fix the delivery instrument 600 to a portion of the myocardium 616 in the area of the hole 614. In this way, leverage or wedging forces may be provided against a distal portion of the piercing member 604 or a delivery instrument 606 or 608 when the physician pushes on a proximal portion of these components.

Referring to FIG. 6B, in some embodiments a delivery instrument 606 may be used to facilitate creating a hole 622 through the myocardium 616. In this example, the delivery instrument 606 is routed through the hole 614 and into the pericardial space P to a desired location on the epicardial surface E. Here, the physician may push the proximal end of the delivery instrument 606 in a distal direction to firmly wedge the delivery instrument 606 in place between the epicardial layer E and an outer pericardial layer 624. Once the delivery instrument 606 is in place, the physician may push the proximal end of the piercing member 610 in a distal direction to force the distal end of the piercing member through the myocardium 616 to create the hole 622.

Referring to FIG. 6C, in some embodiments a delivery instrument 608 includes a side port 626 through which the piercing member 612 may exit to create a hole 628 through the myocardium 616. Again, the delivery instrument 608 is routed through the hole 614 and into the pericardial space P to position the side port 626 at a desired location adjacent the epicardial surface E. Once the delivery instrument 608 is in place, the physician may push the proximal end of the piercing member 612 in a distal direction to force the distal end of the piercing member 612 through the myocardium 616 to create the hole 628.

Referring again to FIG. 2B, once a hole is created from the pericardial space through the myocardium 616, a lead may be routed through the hole into an inner chamber or vasculature of the heart (block 214). For example, in some embodiments the piercing member may include a lumen through which a guidewire may be directed into the inner chamber or vasculature of the heart. The piercing member (and optionally the delivery instrument) may then be withdrawn to enable an introducer and dilator to be routed over the guidewire. As is known in the art, the dilator may be used to widen any of the holes that were created in heart tissue. The introducer (e.g., a sheath) may then be directed through the hole adjacent the inner chamber or vasculature of the heart. Next, the dilator is withdrawn so that the lead may be routed through the sheath and the distal end of the lead positioned in the inner chamber or vasculature of the heart.

As represented by block 216, the lead may then be fixed in place. This may be accomplished, for example, through the use of active or passive fixation means. Once the lead is fixed in place, the sheath and/or guidewire may be removed, leaving the lead implanted in the heart. In some embodiments, to facilitate implant of the lead, the lead may be predisposed to orient to a shape that substantially matches a contour of an epicardial surface of the heart.

FIG. 7 illustrates several embodiments of mechanisms that may be used to fix a lead to heart tissue. For convenience, several fixation members are shown in conjunction with each lead in FIG. 7. It should be appreciated, however, that a given lead may incorporate none of these fixation members, only one fixation member or any combination of these fixation members.

Figure 7C:
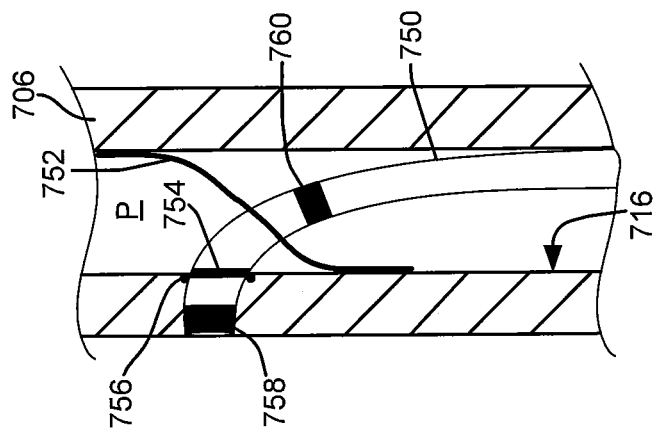
FIG. 7, including FIGS. 7A-7C, consists of several simplified diagrams of various embodiments for fixing a lead to heart tissue.
Figure 7B:
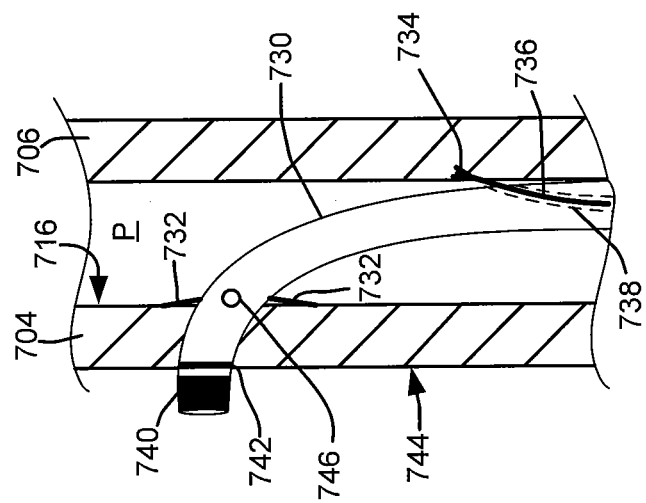
Figure 7A:
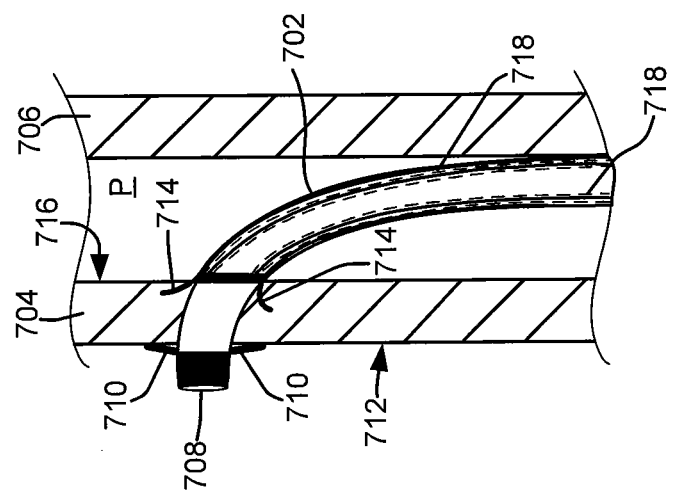

FIG. 7A illustrates a distal portion of a lead 702 that has been routed through the pericardial space P between the myocardium 704 and an outer pericardial layer 706 then through a hole in the myocardium 704. Accordingly, the distal end 708 of the lead 702 may be implanted in an inner chamber or vasculature of the heart. Advantageously, by entering the inner portion of the heart via the pericardial space P, it may be possible to implant the distal end 708 of the lead 702 in virtually any chamber, blood vessel, or other anatomical feature of the heart. For example, the distal end 708 may be implanted in the left atrial chamber, the left ventricular chamber, the right atrial chamber, the right ventricular chamber or some other suitable area of the heart.

A fixation member may be adapted to interact with tissue in different areas of the heart. For example, a fixation member may be positioned on a lead such that the fixation member contacts tissue in the pericardial space P, in a chamber or vasculature or some other tissue.

FIG. 7A illustrates an embodiment where a fixation member 710 is adapted to engage endocardial tissue 712 on a wall of a chamber of the heart. For example, one or more tines or other suitable structure 710 may extend from the lead 702 to stabilize the lead in place after the distal end of the lead has been positioned in the chamber as shown in FIG. 7A.

FIG. 7A also illustrates an embodiment where fixation members 714 are adapted to engage epicardial tissue 716. For example, the fixation members 714 may comprise a helix, tines, barbs, hooks, or some other suitable mechanism that may be directed into and actively hold the lead 702 to the tissue 716.

In some embodiments the fixation members 714 may be adapted to extend from and retract into the lead 702. For example, each fixation member 714 may comprise an elongated member that is adapted to slide within a lumen 718 (as represented by the pairs of dashed lines) in the lead 702. In this way, a physician may retract the fixation member 714 during delivery of the lead, and then deploy the fixation member 714 after the lead 702 has been moved to an implant position. To deploy the fixation member 714, the physician may push a proximal portion (not shown) of the member 714 in a distal direction to force a distal end of the fixation member 714 to extend from a port at a distal end of the lumen 718. The distal end of the fixation member 714 may thus be forced into cardiac tissue (e.g. the epicardium 716) to fix the lead 702 to the tissue.

FIG. 7B illustrates an embodiment where a lead 730 includes fixation members 732 and 734 that are adapted to engage the myocardium 704 (e.g., the epicardial layer 716) and an outer pericardial layer 706. For example, the fixation member 732 may comprise a helix, tines, barbs, hooks, or some other suitable mechanism that may be directed into and actively hold the lead 730 to the tissue 716.

Similarly, the fixation member 734 may comprise a helix, tines, barbs, hooks, or some other suitable mechanism that may be directed into and actively hold the lead 730 to the tissue 706. The fixation member 734 also may be adapted to extend from and retract into the lead 730. For example, the fixation member 734 may comprise an elongated member 736 that is adapted to slide within a lumen 738 (as represented by a pair of dashed lines) in the lead 730. One potential advantage of the fixation member 734 is that it does not engage heart cells of the myocardium. Accordingly, the use of such a fixation member may reduce the risk of damage to heart muscle.

FIG. 7C illustrates an embodiment where a lead 750 includes a fixation member 752 that may comprise a bias mechanism and/or has a relatively large surface area to facilitate fixing the lead 750 in place in the pericardial space P. In some embodiments the fixation member 752 may comprise material that is predisposed to bend in a certain manner. For example, the fixation member 752 may be predisposed to spring away from the lead 750. Once the lead 750 is deployed (e.g., released from a delivery sheath), the fixation member 752 may reorient to its predisposed shape. As shown in FIG. 7C the fixation member 752 may thus be wedged between the epicardium 716 in the outer pericardial layer 706 to hold the lead 750 in place.

Alternatively, in some embodiments the fixation member 752 may comprise a material that may be actively changed in shape. For example, the fixation member 752 may comprise an electrically-active polymer ("EAP") that may take one shape upon application of a voltage and take another shape once the voltage is cut off. In these embodiments, the fixation member 752 may be adapted to be configured in an orientation that facilitates delivery of the lead 750 when voltage is applied. Then, when voltage is cut off, the fixation member 752 may be adapted to orient to an orientation that wedges the lead in place in the pericardial space as shown in FIG. 7C.

In other embodiments the fixation member 752 may comprise a relatively flat material having a relatively large surface area. After the lead 750 is in place the material may be spread out from the lead in the pericardial space (e.g., through the use of a stylet or some other suitable mechanism). In this case, a large portion of the surface area of the fixation member 752 may be wedged between the epicardial layer 716 and the outer pericardial layer 706 in the virtual pericardial space P. That is, in areas of the pericardial space P that are further away from the lead 750, the epicardial layer 716 and the outer pericardial layer 706 will tend to be forced against one another. This, in turn, will tend to hold the fixation member 752 in place thereby holding the lead 750 in place.

FIG. 7C also illustrates an embodiment including a fixation member 754 that is adapted to fix the lead 750 to tissue by application of radio frequency ("RF") energy. For example, the fixation member 754 may comprise an electrode from which a sufficient amount of RF heat energy is emanated such that tissue 756 in the immediate area adheres to the electrode 754 and/or the lead 750.

A variety of fixation mechanisms and techniques may be employed in accordance with the teachings herein. For example, as discussed above active techniques such as hooks, barbs, a helix, rivets, suction mechanisms, adhesive (e.g. biological adhesive) may be employed to fix a lead in place.

Alternatively, or in addition, passive mechanisms may be employed to fix a lead in place. For example, the inherent frictional forces between a lead and the epicardium 716 and the outer pericardial layer 706 may hold a lead in place without the use of any additional fixation mechanisms. In some embodiments, the lead may have a relatively low mass thereby reducing the possibility of micro/macro dislodgment of the lead, while also alleviating irritation of the myocardial surface. In some embodiments, a fixation member (e.g., the fixation member 752 or a fixation member 758) may comprise a material that promotes tissue growth (fibrosis). Such a material may comprise, for example, a polyester such as Dacron or some other suitable material. In this case, the tissue growth may provide mechanical and/or electrical stability for the lead 750. In addition, over time natural body processes may cause tissue (e.g., scar tissue) to form over any fixation member. The lead may thus be fixed in place (or further fixed in place) by such tissue growth.

In view of the teachings herein, it should be appreciated that fixation mechanisms and/or techniques other than those explicitly disclosed herein may be effectively used to fix a lead in place. In addition, a suitable technique may be employed to seal any of the holes that were created through cardiac tissue (e.g., holes 614 and 620). Alternatively, in some cases body processes may effectively seal the holes.

Referring again to FIG. 2B, as represented by block 218 once the lead is fixed in place it may be connected to an implantable cardiac device (e.g. device 100) and placed in service. Thus, for example, the lead may be used to sense activity in the heart and/or to provide cardiac therapy treatment to the heart.

For example, referring to FIG. 7B, the lead 730 may include a sensor 740 such as a pressure sensor that may be used to monitor activity across the myocardium 704. Thus, the sensor 740 may be used to monitor activity in a chamber (e.g., the left ventricle or left atrium). Similarly, the lead 750 in FIG. 7C may incorporate a sensor 760 to monitor activity in the pericardial space. In general, a sensor may be located at any suitable location along a lead.

It should be appreciated that a lead may incorporate one or more of a variety of different types of sensors. For example a sensor may comprise an impedance sensor, a pressure sensor, a motion or acceleration sensor (e.g., any piezoelectric-reactive material), a photoplethysmography-based sensor (e.g., for detecting motion of a heart wall or blood flow) or any other suitable sensor. Such a sensor may be used to detect, for example, heart failure, ischemia or some other condition.

The lead 730 also may include one or more electrodes 742 that may be used to sense electrical signals in and/or provide stimulation therapy (e.g., pacing signals) to nearby cardiac tissue. For example, electrode 742 may be used to sense/stimulate tissue within a chamber (e.g., endocardial tissue 744). In addition, one or more electrodes may be deployed in the pericardial space (e.g., to sense/stimulate the epicardium 716). In general, an electrode may be located at any suitable location along a lead and may be configured in any suitable manner. For example, electrodes may be provided in a unipolar or bipolar configuration. A lead may incorporate one or more shocking electrodes (e.g., in the form of a coil as illustrated in FIG. 1 or in the form of a mesh-based patch).

It should be appreciated based on the teachings herein that a lead may employ one of a variety of configurations. For example, in some embodiments a single lead may incorporate one or more endocardially placed components with endocardial and/or pericardial fixation. In some embodiments a single lead may incorporate pericardially placed components with endocardial and/or pericardial fixation. In some embodiments a single lead may incorporate one or more pericardially and endocardially placed components with endocardial and/or pericardial fixation. In each of these embodiments the components may comprise one or more of a pacing electrode, a sensing electrode, a defibrillation electrode, or a sensor.

In some embodiments one or one or more electrodes may be employed to radiate energy for tissue ablation. For example, RF energy may be supplied to an electrode via the device 100 or some other device and this RF energy may be used to ablate tissue (e.g., to close a blood vessel) near the distal portion (e.g., inside or outside a chamber) of the lead or some other portion of the lead.

In some embodiments, a lead may employ mechanisms to provide other forms of therapy. For example, the lead 730 may include a lumen with one or more ports (hereafter "port 746") that is used to provide a therapy such as a drug, a bio-agent, a biologic therapy or some other suitable therapy to cardiac tissue in the vicinity of the port 746. In some embodiments the port 746 may be used to deliver a steroid, an antibiotic, an anti-arrhythmic (e.g., a β-blocker), an ACE inhibitor, or some other treatment to cardiac tissue. In general, the port 746 may be located at any suitable location along the lead 730 (e.g., epicardially, endocardially or myocardially).

In practice, one or more leads may be implanted in a patient to provide any combination of the above activity sensing and/or therapy capabilities. Accordingly, in some embodiments a portion of the components may be provided on one lead and another portion of the components may be provided on another lead.

Figure 8A:
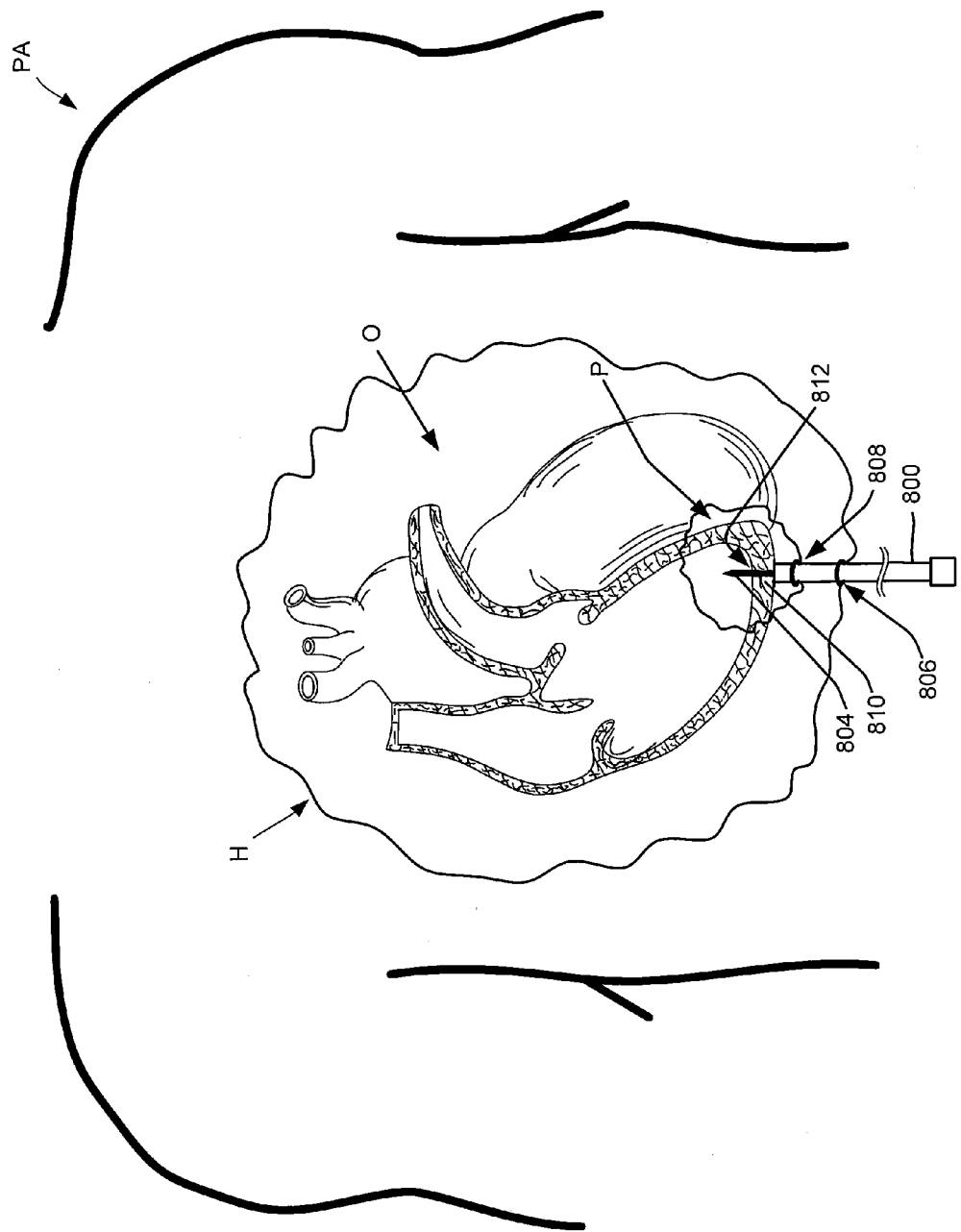
FIG. 8, including FIGS. 8A and 8B, consists of several simplified diagrams of embodiments illustrating a subxiphoid approach for implanting a lead in a heart.
Figure 8B:
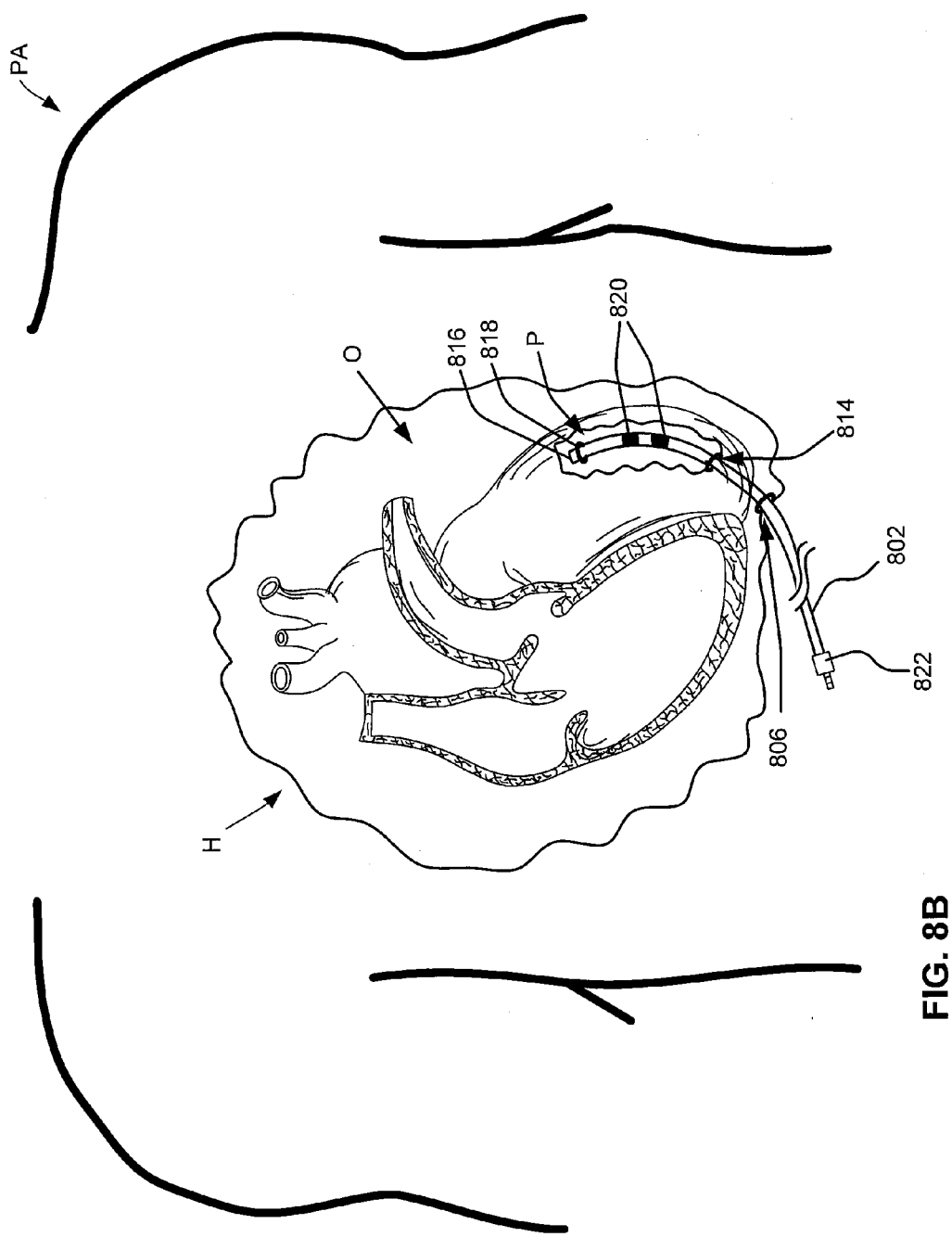
Figure 9:
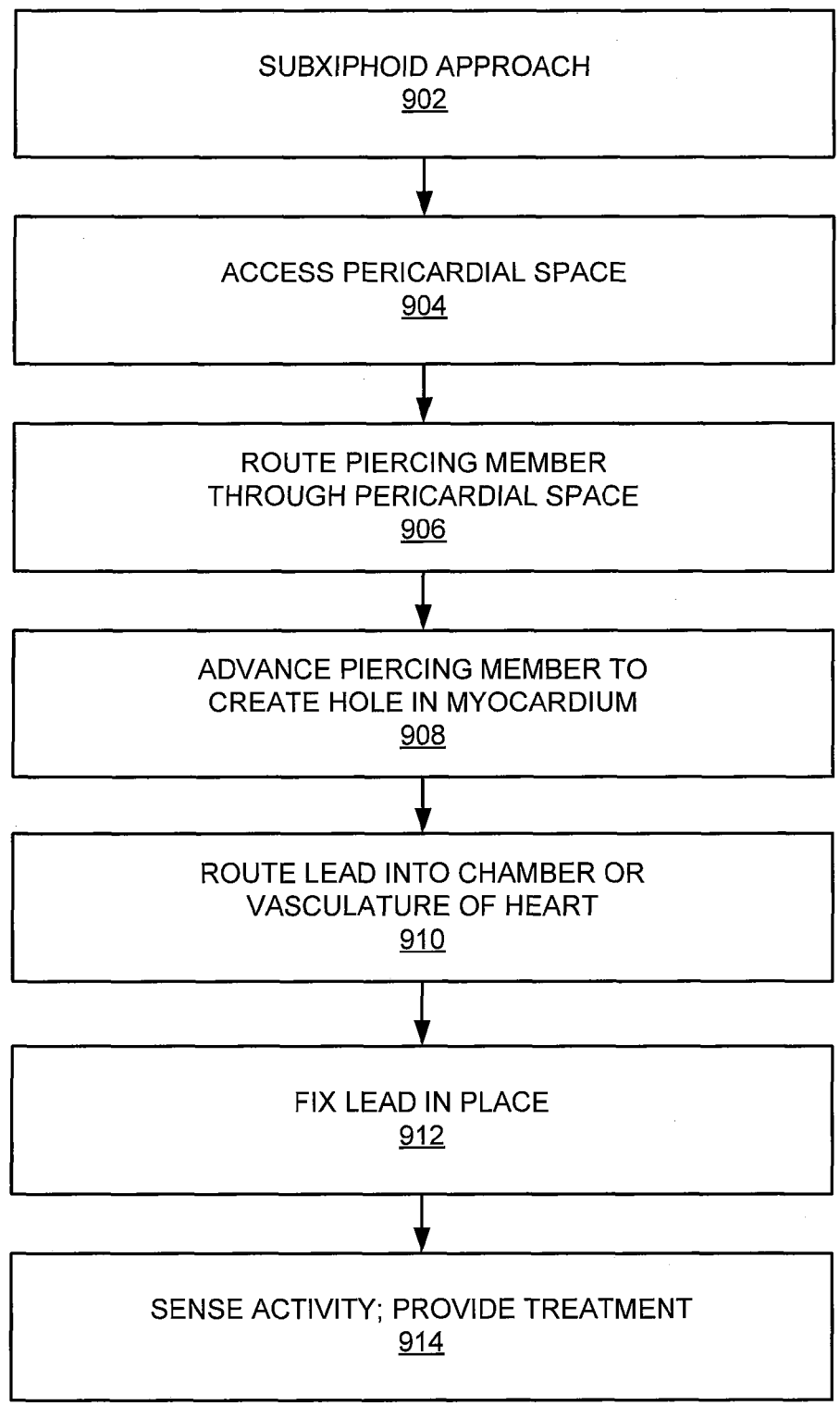
FIG. 9 is a flowchart of an embodiment of operations that may be performed to access the pericardial space and a chamber or vasculature of the heart via a subxiphoid approach.

As discussed above, a variety of techniques may be used to gain access to the pericardial space. FIGS. 8 and 9 illustrate embodiments where a subxiphoid approach may be used to gain access to the pericardial space. FIG. 8A is an example illustrating how a delivery instrument may be used to gain access to an inner chamber or vasculature of the heart via a subxiphoid approach. FIG. 8B is an example illustrating how a lead may be implanted in a patient's body via a subxiphoid approach. FIG. 9 illustrates an embodiment of operations that may be performed in conjunction with a subxiphoid approach. For convenience, the operations of FIG. 9 may be described in conjunction with specific embodiments and/or components described herein. It should be appreciated, however, that these operations may be performed in conjunction with or using other components.

Referring to FIG. 9, as represented by block 902 a physician, surgeon, or electro-physiologist (referred to hereafter for convenience as "the physician") may use a relatively minimally-invasive subcutaneous procedure such as a subxiphoid approach or an intercostal approach to route a lead to the pericardium of a heart of a patient. FIGS. 8A and 8B illustrate in a simplified manner, respectively, a delivery instrument 800 and a lead 802 routed through a pericardial space (represented, in part, by cutout areas P).

Referring to FIG. 8A, a conventional subxiphoid approach may involve routing a needle or other suitable piercing member (hereafter referred to as "the needle") through an incision 806 in a mid-chest area of the patient PA and into the thoracic cavity of the patient PA. The physician routes the needle through the body of the patient PA to the pericardium of the heart H. To improve the clarity of FIG. 8, the heart H shown in the cutout area O is depicted in a simplified and enlarged manner. In practice, one or more incisions 806 may be made in an area below the sternum during the procedure. The location and size of each incision and the types of instruments used during the procedure may vary depending upon the patient's anatomy and the preferences of the physician. Each incision 806 may accommodate a trocar (not shown) for facilitating the insertion and manipulation of one of the instruments.

As represented by block 904, the physician uses the needle to puncture a hole 808 through an outer layer of the pericardium. For convenience, this aspect of the procedure is not explicitly depicted in FIG. 8.

As represented by blocks 906 and 908, the needle 804 may be routed through the pericardial space P to a location on the epicardial surface where a hole is to be created through the myocardium 810 of the heart H. In the example of FIG. 8A, the needle 804 creates a hole 812 through the myocardium 810 and into the right ventricle.

In some embodiments, the delivery instrument 800 (e.g., a sheath-like instrument such as an introducer) may be used in conjunction with creating the hole 808 and/or the hole 812. As an example of the latter case, FIG. 8A illustrates an embodiment where the distal end of the delivery instrument 800 may be positioned against the epicardium. In this case, the delivery instrument 800 may provide stability at a distal portion of a needle 804 when the physician is forcing the needle 804 through the myocardium 810.

To position the delivery instrument 800 as shown in FIG. 8A, the physician may initially advance a guidewire (not shown) through the needle and into the pericardial space. After removing the needle, the physician may route an introducer/dilator (not shown) over the guidewire to enlarge the hole 808 and advance the introducer through the enlarged hole in the pericardium. In some patients it may be necessary to create space for an instrument between the epicardium and the outer pericardial layer. This may be accomplished, for example, via mechanical means, using a vacuum, by injecting a fluid (e.g., saline) into the pericardial space or by some other suitable method. Once the introducer is in place, the dilator (and optionally the guidewire) may be removed. In some embodiments the implanted introducer may function as the delivery instrument 800 or the delivery instrument 800 may be routed through the introducer to the pericardial space.

As represented by block 910, once the hole 812 is created, the physician routes the distal portion of the lead (not shown in FIG. 8A) through the body of the patient PA (e.g., via the introducer), to the pericardial space P and then to the hole 812. The physician then feeds the distal portion of the lead 802 through the hole 812 and manipulates the lead to a desired position. In some embodiments the lead may be routed into the right ventricle outflow tract. Here, one or more electrodes on the lead may be positioned against a wall (e.g., against the septum) of the outflow tract to, for example, pace the heart. Advantageously, the disclosed technique provides a relatively direct route to the outflow tract. Consequently, the lead to the outflow tract may not be subjected to as much manipulation or distortion from the twisting motion of the heart as may be the case with a traditional transvenous approach to the outflow tract.

Various imaging techniques may be used during the implant procedure. In some embodiments, an instrument (e.g., as discussed above) used during implant and/or the lead may include imaging materials or components such as imaging markers that enable the physician to observe the location of the instrument/lead. Here, imaging techniques such as fluoroscopy, echography, MRI, endoscopy, X-ray, ultrasound, MRI, or some other suitable technique may be used to track the location of an instrument/lead within the patient PA. The lead may also utilize certain materials or coatings (e.g., echographic coatings, etc.) to enhance its visibility with these imaging techniques.

As represented by block 912, after the lead is placed at the desired location, an appropriate passive and/or active fixation mechanism may be positioned or deployed to hold the lead in place. This may involve, for example, using one or more of the fixation mechanisms and/or techniques described herein or other suitable mechanisms and/or techniques. The lead may then be connected to an implantable cardiac device (not shown) to provide activity sensing and/or treatment via the lead (block 914).

Through the use of a subxiphoid approach, it may be possible to implant a lead within or upon any chamber or upon any other area of the heart without intrusive surgical techniques and anesthesia that may be required for other implant methods. For example, FIG. 8B illustrates an embodiment where a lead 802 is routed to the left side of the heart for implant. Here, the lead 802 may be implanted instead of or in addition to the lead described above in conjunction with FIG. 8A. That is, in some embodiments one or more leads may be implanted into the heart via a subxiphoid approach. As an example, the lead 802 in FIG. 8B also may be routed through incision 806.

Once the lead 802 is introduced into the body of the patient PA, the lead 802 is manipulated to pass through a hole 814 in the outer pericardial layer. The physician may then manipulate the lead 802 within the pericardial space P to direct the distal end 816 of the lead 802 through a hole 818 in the myocardium. In this way, one or more sensors, electrodes, etc., on the distal end 816 of the lead 802 may be implanted in an inner chamber (e.g., the left ventricle) or vasculature of the heart H. In addition, as discussed above the lead 802 may include one or more sensors, electrodes etc., 820 that may be positioned within the pericardial space. Once the lead 802 is fixed in place, the lead may be connected to an implantable cardiac device (not shown) via a connector 822.

The techniques described herein may be used in a wide variety of applications. For example, FIGS. 10-13 illustrate several embodiments relating to implanting a mechanical constriction member in the heart. In some applications a mechanical constriction member may be used to maintain or change the geometry of the heart. Accordingly, in some embodiments a mechanical constriction member may be used to prevent or reduce dilation of heart tissue that may be associated with cardiac heart failure, myocardial infarction, an aneurysm or some other condition that may tend to dilate heart tissue.

Figure 10:
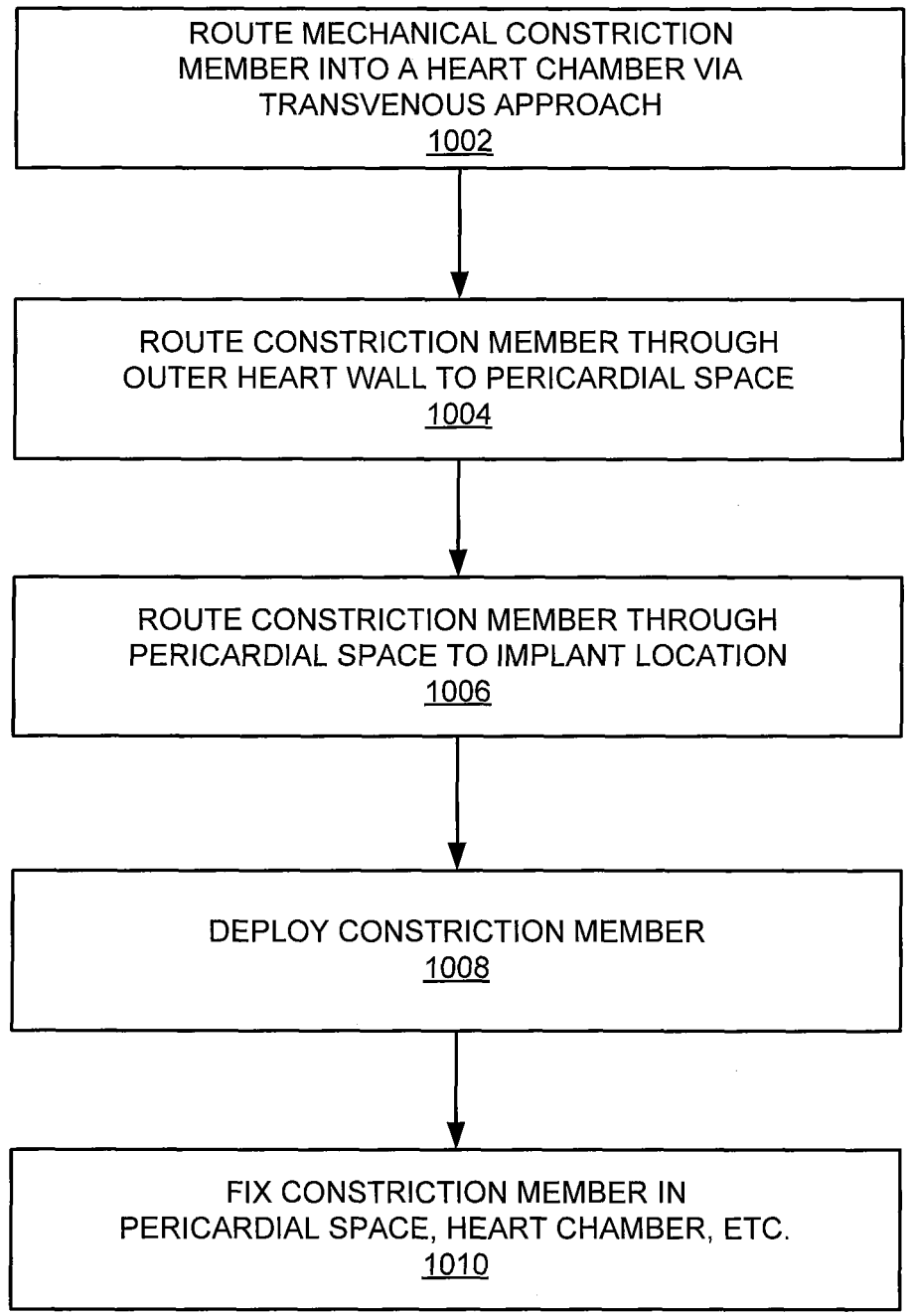
FIG. 10 is a flowchart of an embodiment of operations that may be performed to deploy a mechanical constriction member over a portion of the heart.

FIG. 10 illustrates an embodiment of operations that may be performed to implant a mechanical constriction member, e.g., patch, net, harness, sock, etc., in or on the heart or around a portion of the heart. For convenience, the operations of FIG. 10 may be described in conjunction with specific embodiments and/or components described herein. It should be appreciated, however, that these operations may be performed in conjunction with or using other components.

As represented by block 1002, a mechanical constriction member may be adapted to be routed through the venous return system of a patient. For example, referring to FIG. 11A, a mechanical constriction member 1100 (represented by the dashed lines) may be adapted to fold such that it may lie against a lead or some other delivery instrument that may be routed through, for example, an implantable sheath 1102.

Figure 11B:
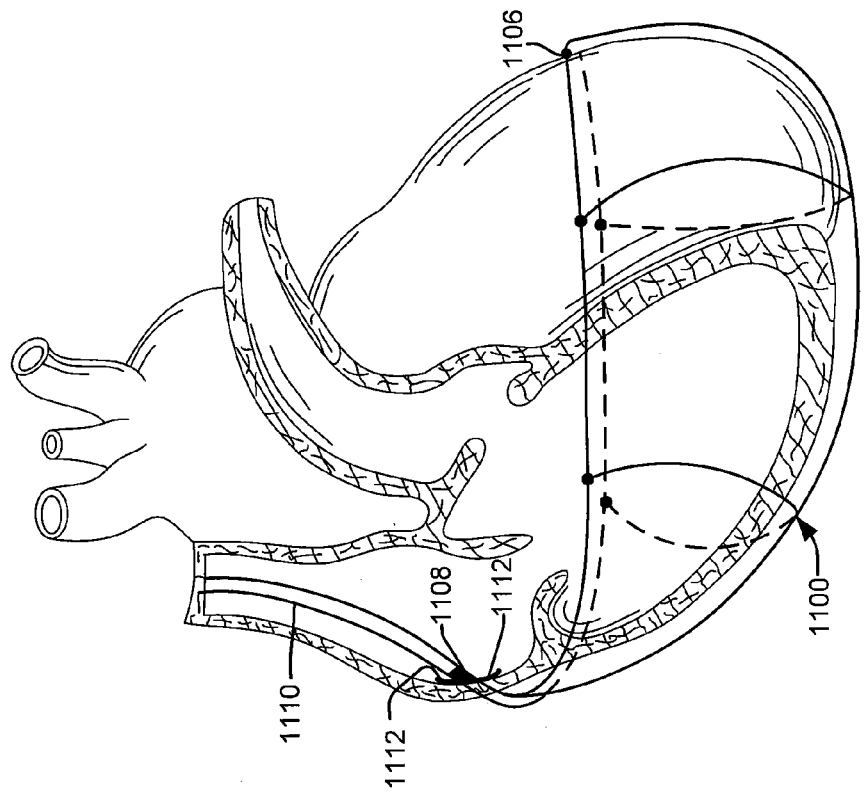
FIGS. 11A and 11B, is a simplified diagram of an embodiment of a mechanical constriction member adapted to be deployed over a portion of the heart.
Figure 11A:
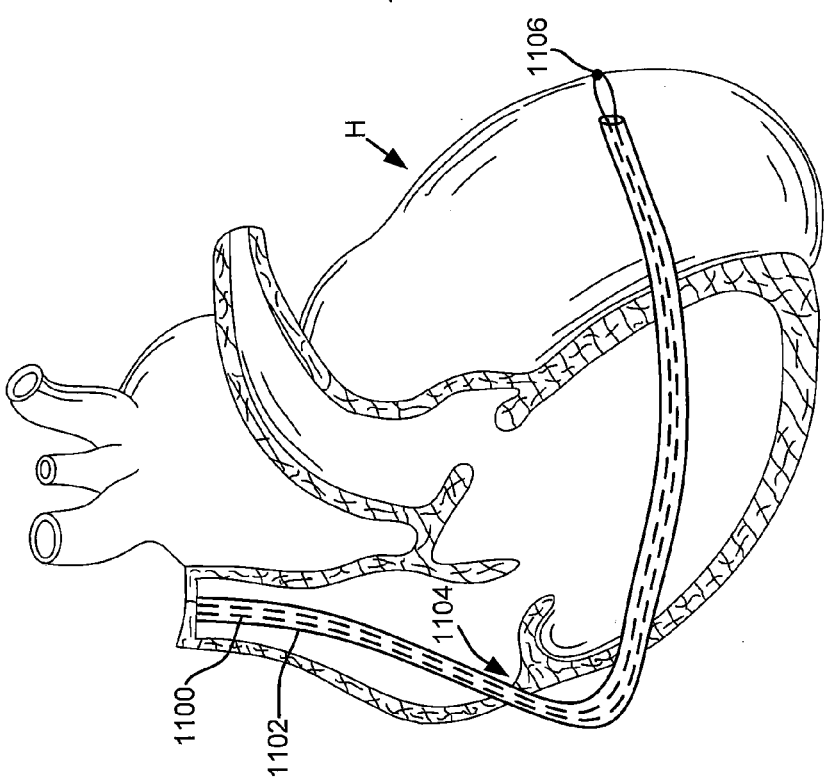

As represented by block 1004, a physician may route the constriction member 1100 through an outer wall of the heart H and into the pericardial space (e.g., using one of the techniques described herein). In the example of FIG. 11A, the sheath 1102 carrying the constriction member 1100 was routed through a hole 1104 in an outer wall of the right atrium.

As represented by block 1006, the physician routes the constriction member 1100 through the pericardial space to a desired implant location. In FIG. 11A, the sheath 1102 carrying the constriction member 1100 was routed around the pericardial space to position the distal end of the constriction member 1100 across the heart H.

As represented by block 1008, the physician then deploys the constriction member 1100 on the heart H. This may involve, for example, fixing at least a portion of the constriction member 1100 to cardiac tissue. In FIG. 11A, the distal end of the constriction member 1100 may be attached to the epicardial surface of the heart H to help hold the constriction member 1100 in place once it is deployed. This fixation may be achieved using any suitable fixation mechanism or technique (e.g., a screw, a hook, a barb, etc.) 1106.

Next, the physician may release the constriction member 1100 from the sheath 1102. For example, the sheath may be withdrawn in a proximal direction while the constriction member 1100 is held in place via, for example, the fixation mechanism 1106 or a stylet.

If applicable, a physician unfolds the constriction member 1100 within the pericardial space. For example, FIG. 11B illustrates an embodiment where the constriction member 1100 takes the form of a lariat or net-like structure. In this case, the physician may manipulate the individual strands of the constriction member 1100 within the pericardial space such that the constriction member 1100 wraps around a portion of the heart H. This may be accomplished, for example, through the use of a stylet or other suitable mechanism.

As represented by block 1010, the physician then fixes the constriction member 1100 within the heart H. In the embodiment of FIG. 11B the constriction member 1100 may include a tightening mechanism 1108 (e.g., similar to a noose of a lariat) that serves to tighten the deployed portion of the constriction member 1100 around the heart H. For example, the physician may pull on a proximal portion of a cable 1110 of the constriction member 1100 which, in turn, pulls the deployed portion of the constriction member 1100 against epicardium. The tightening mechanism 1108 may then serve to hold the deployed portion of the constriction member 1100 in this position.

In some embodiments the constriction member 1100 also may include a mechanism to prevent the deployed portion of the constriction member 1100 from moving in the distal direction. For example, one or more fixation members 1112 that extend from the constriction member 1100 may engage or otherwise be affixed to cardiac tissue. The fixation members 1112 may comprise, for example, a fixation mechanism as described herein (e.g., tines, a screw, hooks, barbs, etc.). In the example of FIG. 11B, the fixation members 1112 engage endocardial tissue at an outer wall of the right atrial chamber.

Figure 12:
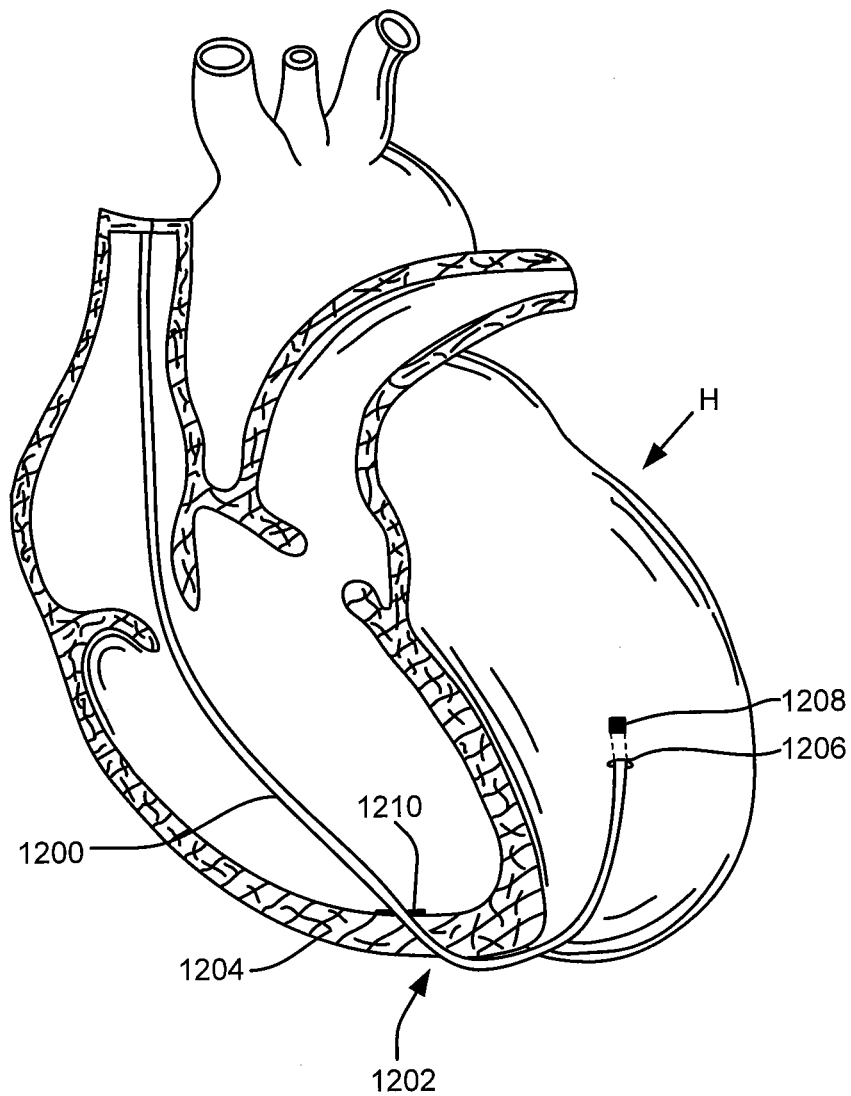
FIG. 12 is a simplified diagram of an embodiment of a linear mechanical constriction member implanted in the heart.

A mechanical constriction member may take a variety of forms and may be implanted within the heart in a variety of ways. For example, a constriction member may be implanted into the pericardial space using any of the techniques described herein or using other suitable techniques. In addition, FIG. 12 illustrates an embodiment of a linear mechanical constriction member 1200 that is implanted into an inner chamber or vasculature of the heart.

The constriction member 1200 also may be implanted using one or more of the techniques described herein. In FIG. 12, the constriction member 1200 is initially implanted transvenously into the right ventricular chamber. Next, the constriction member 1200 is routed through a hole 1202 in an outer wall 1204 of the heart H and into the pericardial space. The distal end of the constriction member 1200 is then routed through a hole 1206 in the myocardium and into, in this example, the left ventricle. The distal end of the constriction member 1200 may be fixed within the chamber. This fixation may be achieved using any mechanism or technique discussed herein or any other suitable fixation mechanism or technique (e.g., a hook, a barb, etc.) 1208. Accordingly, the constriction member 1200 may be tightened by pulling a proximal portion (not shown) of the constriction member in a proximal direction.

As discussed above in conjunction with FIG. 11, the constriction member 1200 also may include a mechanism to prevent the deployed portion of the constriction member from moving in the distal direction. For example, one or more fixation members 1210 that extend from the constriction member 1200 may engage or otherwise be affixed to cardiac tissue (e.g., endocardial tissue at an outer wall of the right ventricular chamber).

FIG. 13 illustrates an embodiment where a mechanical constriction member 1300 is deployed over heart tissue. For example, the constriction member 1300 may be deployed in the pericardial space. In this way, the constriction member may prevent or reduce dilation of cardiac tissue associated with, for example, an aneurysm or a myocardial infarction.

Figure 13A:
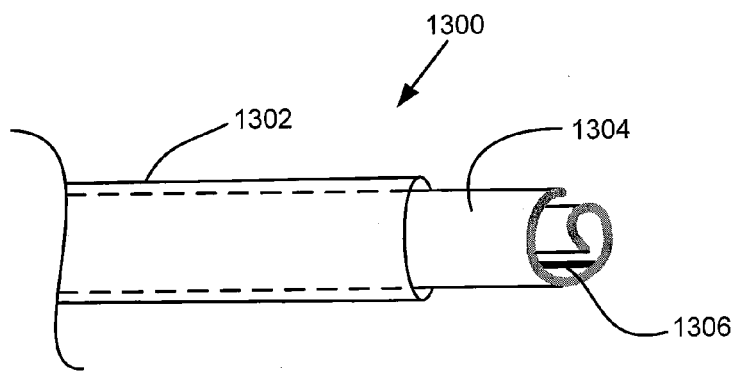
FIGS. 13A and 13B, is a simplified diagram of an embodiment of a mechanical constriction member adapted to be deployed over a portion of the heart.

As illustrated in FIG. 13A, the constriction member 1300 may be adapted for transvenous implant. For example, the constriction member 1300 may be adapted to be folded or rolled up for placement in a delivery instrument such as a sheath 1302 that may be routed through the venous system. The constriction member 1300 may include a flexible deployable portion 1304 that, for example, may be unfolded to a relatively flat orientation upon implant. In some embodiments the deployable portion 1304 may be comprised of a mesh or other material suitable for constraining cardiac tissue. The constriction member 1300 also may include a thin elongated member 1306 that enables a physician to manipulate the position of the deployable portion 1304 during implant.

Figure 13B:
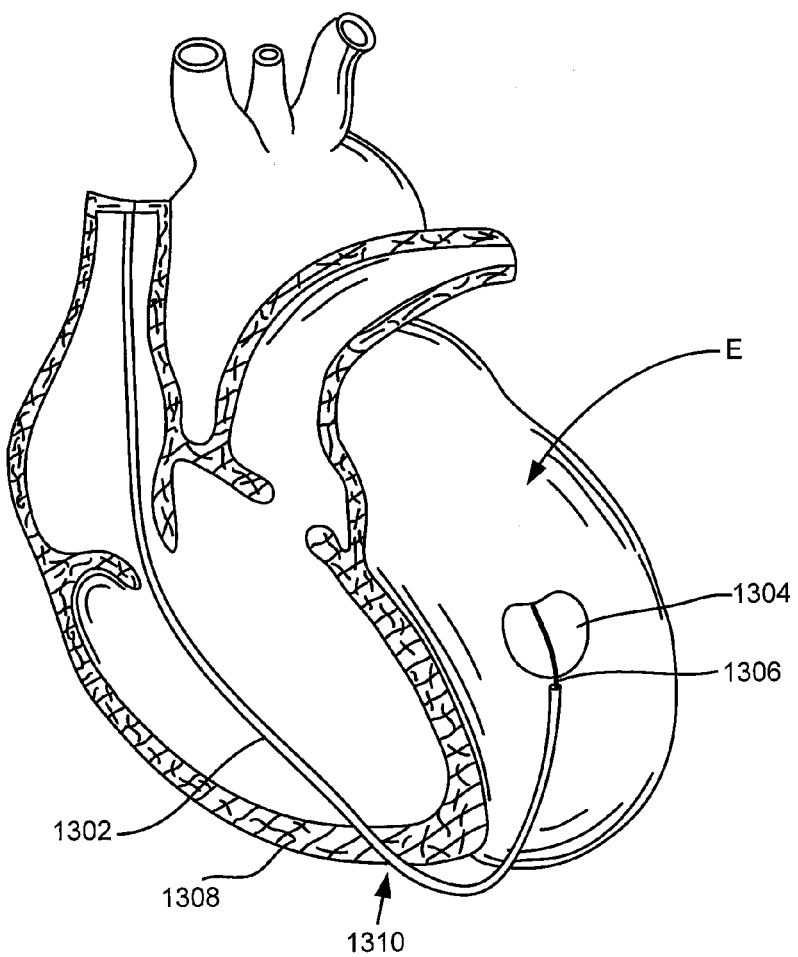

Referring now to FIG. 13B, a physician may implant the constriction member 1300 using one or more techniques described herein. For example, a physician may initially route the constriction member 1300 through a vein and into the right ventricular chamber (e.g., via the sheath 1302). The physician may then route the distal portion of the constriction member 1300 through a hole 1310 in an outer wall 1308 of the heart H and into the pericardial space.

Next, the distal portion of the constriction member 1300 may be manipulated to position the constriction member 1300 over heart tissue (e.g., the epicardium) above a portion of the heart inflicted with a myocardial infarction. The physician may then deploy (e.g., unfold or unroll) the deployable portion 1304 such that the deployable portion covers the heart tissue above the myocardial infarction.

In some embodiments of the constriction member 1300 may be fixed in place. This fixation may be achieved using any mechanism or technique discussed herein or any other suitable fixation mechanism or technique (e.g., an adhesive, a hook, a barb, etc.). At this point, the sheath 1302 may be removed and, in some embodiments, the member 1306 may be removed.

It should be appreciated from the above that the various structures and functions described herein may be incorporated into a variety of apparatuses (e.g., a lead, a delivery apparatus, etc.) and implemented in a variety of ways. In addition, it should be appreciated that various types of components may be incorporated into an implantable lead in accordance with the teachings herein. For example, a lead and a delivery instrument may be constructed of a conventional biocompatible lead material such as silicone, polyurethane or any other suitable material. The electrodes of the electrode modules may be constructed of a conventional electrode material such as platinum-iridium or any other suitable electrode material. A piercing member, a guidewire, a delivery instrument, a constriction member, a fixation mechanism and other components as taught herein also may be constructed using implantable metals such as MP35N, Nitinol or some other suitable material. Some of the components may be coupled or connected using adhesives, mechanical restraint, welding, bonding or using some other suitable technique. It also should be appreciated that other types of implementation techniques may be used to provide an implantable lead in accordance with the teachings herein.

The components and functions described herein may be connected and/or coupled in many different ways. The manner in which this is done may depend, in part, on whether and how the components are separated from the other components. In some embodiments some of the connections and/or couplings represented by the lead lines in the drawings may be implemented as discrete wires or in other ways.

The signals discussed herein may take several forms. For example, in some embodiments a signal may comprise electrical signals transmitted over a wire, light pulses transmitted through an optical medium such as an optical fiber or air, or RF waves transmitted through a medium such as air, etc. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

While certain exemplary embodiments have been described above in detail and shown in the accompanying drawings, it is to be understood that such embodiments are merely illustrative of and not restrictive of the broad invention. In particular, it should be recognized that the teachings herein apply to a wide variety of apparatuses and methods. It will thus be recognized that various modifications may be made to the illustrated and other embodiments described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A transpericardial method of accessing an interior of a heart, comprising:

routing a distal portion of an implantable cardiac lead into a pericardial space of the heart, wherein routing a distal portion of an implantable cardiac lead into a pericardial space comprises routing the distal portion of the lead from an interior chamber of the heart through myocardial tissue and into the pericardial space, wherein routing a distal portion of an implantable cardiac lead into a pericardial space of the heart comprises using a piercing member to create a hole for the lead through the myocardial tissue from the interior chamber to the pericardial space, and wherein the piercing member comprises a spring that expands from a distal end of the piercing member as the piercing member passes into the pericardial space;

sensing electrical signals via an electrode of the spring to determine when the spring passes into the pericardial space; and routing the distal portion of the lead from the pericardial space through myocardial tissue and into a chamber or vasculature of the heart.

2. The method of claim 1 wherein routing the distal portion of the lead from an interior chamber of the heart through myocardial tissue comprises routing the distal portion of the lead through a vein to the interior chamber, wherein the interior chamber comprises a right ventricle.

3. The method of claim 1 wherein routing the distal portion of the lead from the pericardial space through myocardial tissue and into a chamber or vasculature of the heart comprises creating a hole through the myocardial tissue and into the chamber or vasculature using the piercing member that is adapted to curve from the interior chamber through the pericardial space to the chamber or vasculature.

4. The method of claim 1 wherein routing a distal portion of an implantable cardiac lead into a pericardial space comprises routing the distal portion of the lead through a heart wall in the vicinity of an apex of the right ventricle.

5. The method of claim 1 further comprising fixing the distal portion of the lead to one or more of tissue of an inner surface of the chamber or vasculature, tissue of an epicardial layer and tissue of an outer pericardial layer of the heart using a fixation member, wherein the fixation member comprises at least one of the group consisting of: a barb, a hook, a helix, an adhesive, a rivet, a suction mechanism, a material that promotes tissue growth, and an RF electrode adapted to provide RF energy to the tissue, a bias mechanism, and an electrically-active polymer.

6. The method of claim 1 comprising creating a hole in the myocardial tissue using a delivery instrument that curves to direct a piercing member toward the myocardial tissue.

7. The method of claim 1 wherein routing the distal portion of the lead from the pericardial space through myocardial tissue and into a chamber or vasculature of the heart comprises positioning the distal portion of the lead through the myocardial tissue such that at least a portion of an electrode and/or a sensor on the distal portion of the lead is implanted within the chamber or vasculature.

8. The method of claim 7 wherein positioning the distal end of the lead further comprises positioning the distal portion such that at least a portion of an electrode and/or sensor proximal the distal portion is implanted within the pericardial space.

* * * * *